US00PP35877P2

(12) United States Plant Patent
Korlipara

(10) Patent No.: US PP35,877 P2
(45) Date of Patent: Jun. 18, 2024

(54) ***KNIPHOFIA* PLANT NAMED 'POCO DAYBREAK'**

(50) Latin Name: *Kniphofia spp.*
Varietal Denomination: Poco Daybreak

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 59 days.

(21) Appl. No.: 18/112,109

(22) Filed: Feb. 21, 2023

(51) Int. Cl.
*A01H 5/02* (2018.01)
*A01H 6/00* (2018.01)

(52) U.S. Cl.
USPC ..... Plt./443
CPC ..... *A01H 6/00* (2018.05)

(58) Field of Classification Search
USPC ..... Plt./443
CPC ..... A01H 5/02
See application file for complete search history.

(56) References Cited

PUBLICATIONS https://www.facebook.com/TerraNovaNurseriesInc/posts/kniphofia-poco-daybreak-is-another-great-addition-to-the-poco-series-of-kniphofi/5434182253293145/; May 19, 2022; 1 page.*
https://www.bfgsupply.com/media/6179/2022-2023-terra-nova-product-program.pdf; Jun. 8, 2023; 4 pages.*
https://www.canr.msu.edu/hrt/our_gardens/Visit/Amien-and-Florence-Carter-Trial-Garden/2022%20Trial%20Booklet; Jun. 9, 2023; 41 pages.*

* cited by examiner

*Primary Examiner* — Kent L Bell
(74) *Attorney, Agent, or Firm* — The Webb Law Firm

(57) ABSTRACT

A new and distinct *Kniphofia* plant characterized by its habit of forming multiple crowns fast and each crown produces inflorescences in the first season, inflorescences of bicolored coral-orange and yellow flowers on short stems, a very long bloom time with repeat blooming, a short habit, excellent vigor, and narrow, grassy, and short leaves.

2 Drawing Sheets

Botanical classification: *Kniphofia* spp.
Varietal denomination: 'Poco Daybreak'.

BACKGROUND OF THE NEW PLANT

The present invention is a new and distinct *Kniphofia* plant having the varietal name 'Poco Daybreak'. *Kniphofia* is in the family Xanthorrhoeaceae. 'Poco Daybreak' is a hybrid of the species *uvaria*, resulting from a planned breeding program with the purposes of producing short, compact, and reblooming *Kniphofia* plants. The cross occurred as a result of open pollination in a cultivated field located in Canby, Oregon of *Kniphofia* plant K58-3 (unpatented), as the seed parent, amongst a collection of *Kniphofia* plants as the possible pollen parent. Accordingly, the exact identity of the pollen parent is unknown. The pollination is estimated to have taken place in the month of June or July in 2017. The new cultivar, 'Poco Daybreak', was selected for having the best habit, flower color, reblooming quality, crown count, and unusally large inflorescences from many seedlings of the cross in Canby, Oregon.

Compared to *Kniphofia* plant K58-3, the seed parent, the new cultivar is shorter, more free-flowering, has much larger floral racemes and a more distinct bicolored red to yellow color shift as the flowers age.

Compared to *Kniphofia* plant named 'Poco Sunset' (U.S. Plant Pat. No. 28,464), the new cultivar is shorter with shorter leaves in a denser habit. The flowers of the new cultivar are more coral-orange and yellow rather than coral-red, shifting to bright yellow and cream.

Compared to *Kniphofia* plant named 'Fire Glow' (U.S. Plant Pat. No. 22,894), the new cultivar has shorter leaves and inflorescences and has flowers that are coral-orange and yellow rather than red-orange and coral.

The new variety has only been reproduced by asexual propagation (leaf cuttings, division, and tissue culture), beginning in July of 2018. Each of the progeny exhibits identical characteristics to the original plant. Asexual propagation by leaf cuttings, division, and tissue culture performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Kniphofia* plants known to the breeder, the new variety is characterized by the following:

1. Forming multiple crowns fast, with each crown producing inflorescences in the first season;
2. Large inflorescences of bicolored coral-orange and yellow flowers on short stems;
3. A very long bloom time with repeat blooming from July through October in Canby, Oregon;
4. A short habit;
5. Narrow, short, and grassy leaves; and
6. Excellent vigor.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
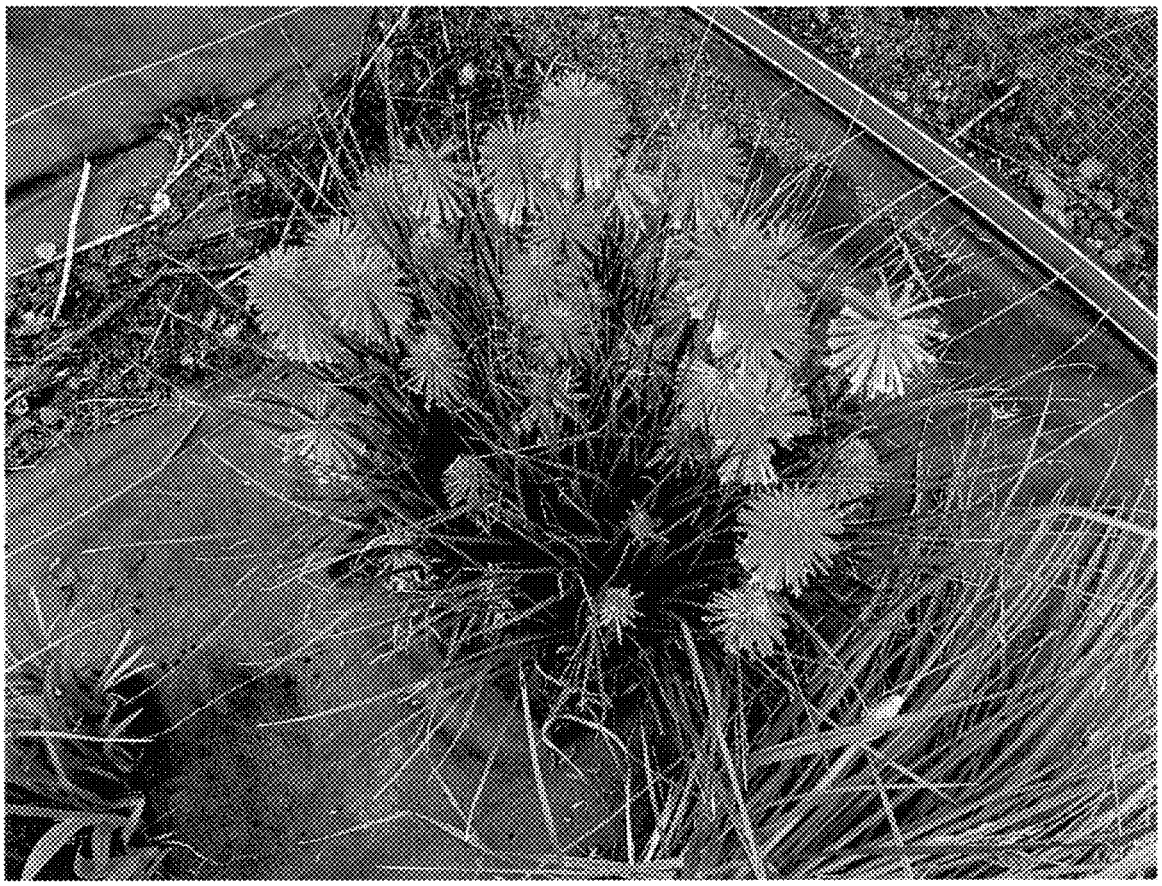
FIG. 1 illustrates a mature plant of the new variety in Canby, Oregon in July.
Figure 2:
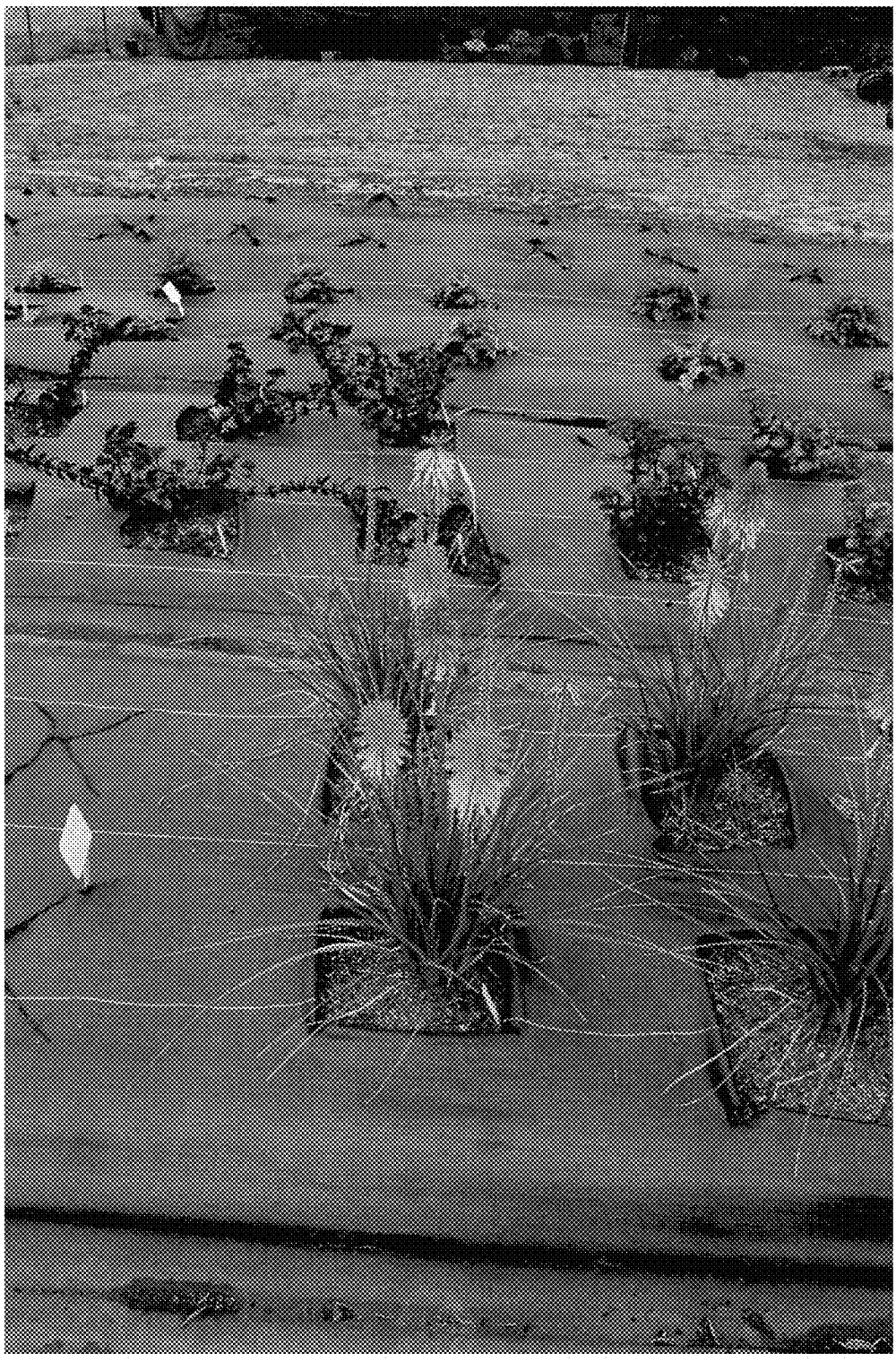
FIG. 2 illustrates an 8-month-old plant of the new variety in Canby, Oregon in August.

The following is a detailed description of the new variety based on observations of 9-month-old plants in late September that were grown outside in full sun in field conditions in Canby, Oregon (USDA Zone 8). Temperatures range from a high of 35° C. in August to an average of 0° C. in January. Normal rainfall in Canby, Oregon is around 1 m per year. Color references are based on The 2007 R.H.S. Colour Chart of The Royal Horticultural Society of London, $5^{th}$ Edition.

Plant:

*Type*.—Rhizomatous herbaceous perennial.
*Hardiness*.—USDA Zones 7 to 9.
*Size*.—28.0 to 34.0 cm wide and 38.0 to 40.0 cm tall from the top of the soil to the top of the inflorescences.
*Crown number*.—About 21.
*Leaves per crown*.—About 12.
*Inflorescences per crown*.—1 to 3.
*Form*.—Clumping.
*Vigor*.—Excellent.

Leaf:

*Type*.—Simple.
*Leaf arrangement*.—Basal rosette.
*Shape*.—Strap-like, keeled.
*Length*.—29.0 to 35.0 cm.
*Width*.—6.0 to 8 mm (measured near the base).
*Margin*.—Entire.
*Apex*.—Acuminate.
*Base*.—Clasping.
*Texture*.—Glabrous on both sides.
*Upper surface color*.—RHS 139B.
*Lower surface color*.—RHS 139B.
*Venation*.—Parallel.

Inflorescence:

*Type*.—Spike-like scapose raceme.
*Flower number per raceme*.—About 135.
*Length*.—23.5 cm.
*Width*.—7.5 cm.
*Bloom period*.—July through October in Canby, Oregon.
*Lastingness*.—From 2-4 weeks on the plant depending on weather and the temperature.
*Peduncle*.—Length: 26.0 cm. Width: 9.0 mm. Texture: Glabrous. Color: RHS 147B.
*Pedicel*.—Length: 2.5 mm. Diameter: 1.0 mm. Texture: Glabrous. Color: RHS 173B.

Flower bud:

*Length*.—25.0 mm.
*Width*.—6.0 mm.
*Texture*.—Glabrous.
*Color*.—RHS N34B.

Flower:

*Type*.—Actinomorphic.
*Shape*.—Cylindrical and tubular.
*Depth*.—29.0 mm.
*Width*.—12.0 mm.
*Texture*.—Waxy, with a glabrous surface on both sides.
*Fragrance*.—None.
*Corolla*.—Length: 30.0 mm. Width: 12.0 mm. Arrangement: 6-lobed, fused tepals. Tube size: 28.0 mm long and 8.0 mm wide. Lobes: Shape: Reflexed, ovate, entire, and acute. Size: 4.0 mm long and 3.0 mm wide. Color: Inside RHS 28B, outside RHS 21C on the lower flowers to RHS 31B.
*Pistil*.—Number: 1. Length: 26.0 mm. Ovary size: 2.5 mm long and 1.5 mm wide. Ovary color: RHS 146D. Style length: 23.0 mm. Style color: RHS N167D. Stigma color: RHS 173A.
*Stamen*.—Number: 6. Length: 31.0 mm. Filament length: 28.0 mm. Filament color: RHS 145C. Anther length: 1.0 mm. Anther color: RHS 22A. Pollen amount: Slight. Pollen color: RHS 8C.

Fruit/seeds: No mature fruit formed and no seeds produced.

Pests/diseases: No unusual resistance or susceptibility noted to date.

I claim:

1. A new and distinct variety of *Kniphofia* plant named 'Poco Daybreak', substantially as illustrated and described herein.

* * * * *